US006214594B1

(12) United States Patent
Markland et al.

(10) Patent No.: US 6,214,594 B1
(45) Date of Patent: Apr. 10, 2001

(54) SIZE ENHANCED FIBRINOLYTIC ENZYMES: LIMITATIONS OF PLASMA INACTIVATION

(75) Inventors: Francis S. Markland, Manhattan Beach; Stephen D. Swenson, Arcadia, both of CA (US)

(73) Assignee: University of California, Los Angeles, CA (US)

( * ) Notice: Subject to any disclaimer, the term of this patent is extended or adjusted under 35 U.S.C. 154(b) by 0 days.

(21) Appl. No.: 09/306,150

(22) Filed: May 6, 1999

Related U.S. Application Data
(60) Provisional application No. 60/084,833, filed on May 8, 1998.

(51) Int. Cl.[7] .......................... C12N 11/06; C12N 11/10; C12N 11/12; C12N 11/08; C12N 9/96; C12N 9/48
(52) U.S. Cl. .................. 435/181; 435/178; 435/179; 435/180; 435/212; 435/188
(58) Field of Search ................................. 435/178, 179, 435/180, 181, 212, 188

(56) References Cited

U.S. PATENT DOCUMENTS

| 4,378,435 | 3/1983 | Tagagi et al. | 435/180 |
|---|---|---|---|
| 4,378,803 | 4/1983 | Tagagi et al. | 604/280 |
| 4,446,316 | 5/1984 | Chazov et al. | 536/112 |
| 4,610,879 | 9/1986 | Markland, Jr. et al. | 424/94 |
| 4,640,835 | 2/1987 | Shimizu et al. | 424/94 |
| 4,935,465 | 6/1990 | Garman | 525/54.1 |
| 5,234,903 | 8/1993 | Nho et al. | 514/6 |
| 5,514,572 | 5/1996 | Veronese et al. | 435/180 |

FOREIGN PATENT DOCUMENTS 0183503   6/1986   (EP) .

OTHER PUBLICATIONS

Baramova, E.N., et al., Biochemistry, 29:1069–1074 (1990).
Clark, R., et al., Journal of Biological Chemistry, 271(36):21969–21977 (1996).

*Primary Examiner*—Jon P. Weber
(74) *Attorney, Agent, or Firm*—Fulbright & Jaworski L.L.P.

(57) ABSTRACT

A size modified fibrinolytic enzyme, wherein the size of the enzyme is modified by covalent attachment of at least one large organic molecule to the enzyme.

14 Claims, 4 Drawing Sheets

SIZE ENHANCED FIBRINOLYTIC ENZYMES: LIMITATIONS OF PLASMA INACTIVATION

CROSS-REFERENCE TO RELATED APPLICATIONS

Figure 1:
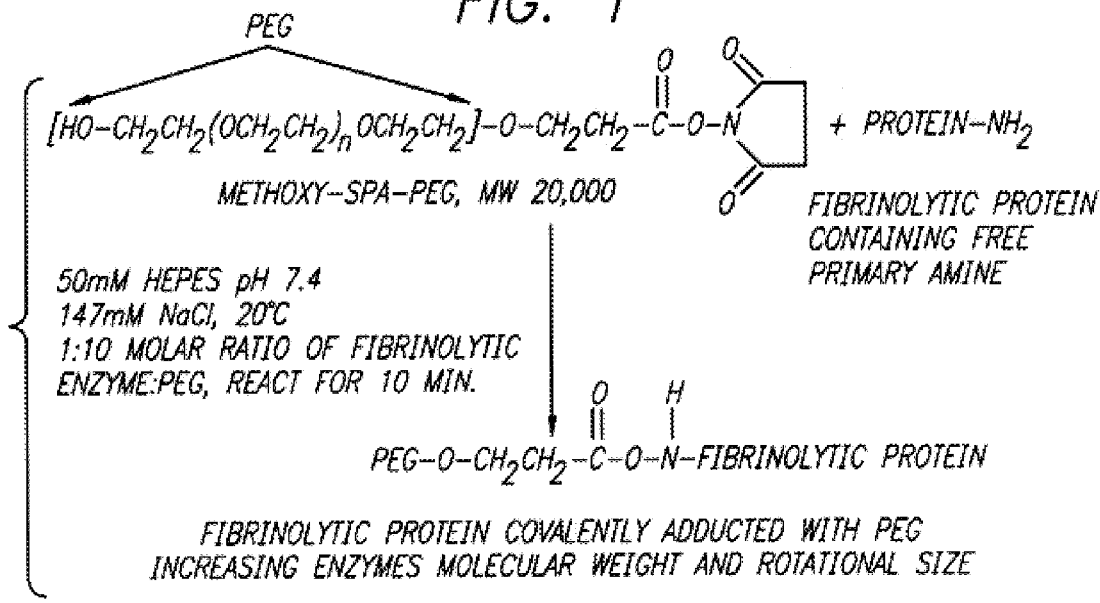

This application claims the benefit of the U.S. Provisional Patent Application Serial No. 60/084,833 filed May 8, 1998.

TECHNICAL FIELD OF THE INVENTION

The present invention relates generally to the field of biochemistry and in particular to size modification of a fibrinolytic enzyme.

BACKGROUND OF THE INVENTION

Fibrolase is a metalloproteinase isolated from the venom of the southern copperhead (*Agkistrodon contortrix contortrix*). It is typical of the small venom metalloproteinases of approximately 23 kDa. The enzyme possesses proteolytic activity directed to the cleavage of the α- and β-chains of fibrin and fibrinogen. In that fibrin is a major component of occlusive thrombi, the degradative action of fibrolase leads to thrombus lysis and elimination. Fibrinolytic activity of fibrolase has been examined in both test tube and animal models. The enzyme has been shown to effectively lyse fibrin clots in-vitro [Guan, A. L., et al., *Arch. Biochem. Biophys.*, 289:197–207 (1991)] and in-vivo [Markland, F. S., et al., *Circulation*, 90:2448–2456 (1994); Markland, F. S., in *Natural Toxins II* (Singh, B. R. and Tu, A. T., eds.), pp 427–438, Plenum Press, New York (1996)]. While fibrolase can degrade mature thrombi it has no effect on the formation of these structures.

Although fibrolase degrades fibrin(ogen) in the test tube, in the circulation the enzyme is efficiently inactivated by alpha-2 macroglobulin (α2M). To enable complete thrombus dissolution in vivo a modification to fibrolase must be made to block its rapid inactivation by α2M. α2M is a general protease inhibitor present in the circulatory system at fairly high concentrations (≅3 μM). This inhibitor has the ability to bind to and sequester small proteases and remove them from the circulation via the formation of a covalent bond between the proteinase and the very large, 720 kDa, tetrameric inhibitor molecule. Interactions between proteinases and α2M are sterically influenced and appear to be directly related to the size of the proteinase [Werb, Z., et al., *Biochemical Journal*, 139:359–368 (1974)]. A 68 kDa hemorrhagic metalloproteinase from Crotalus atrox is not inhibited by α2M, while another closely related but smaller, 23 kDa, metalloproteinase is rapidly and effectively bound and inhibited by α2M [Baramova, E. N., et al., *Biochemistry*, 29:1069–1074 (1990)]. Once bound to α2M the proteinase is essentially removed from circulation, unable to act on the target molecule, in the case of fibrolase, a thrombus.

SUMMARY OF THE INVENTION

In accordance with this invention, a fibrinolytic enzyme, fibrolase, is modified by covalent attachment with a water soluble large organic molecule which alters the size of fibrolase while not changing the effectiveness of its thrombolytic activity. The size modified fibrolase, due to its increased bulk and rotational size, can interact with α2M with much slower kinetics and thus have a longer active circulatory half-life. Slowing the interaction of fibrolase with α2M allows for more rapid and effective thrombolysis by the fibrinolytic enzyme and at lower administered dosage.

Size modification of the fibrinolytic enzyme (including, but not limited to, fibrolase or similar fibrinolytic enzymes from the Crotalus or Agkistridon species, such as the fibrinolytic enzyme from *A. piscovirus conanti* [Retzios, A. D., et al., *Protein Expressing Purification,* 1(1):33–39 (1990)] or from *C. basiliscus basiliscus* [Retzios, A. D., et al., *Protein Expressing Purification,* 1(1):33–39 (1990); Retzios, A. D. et al., *Biochemistry,* 31:4547–4557 (1992)] or enzymes isolated from other living organisms) can be made via a number of different methods. The adducted groups can be any chemically inert large water soluble non-charged organic molecule, having a molecular weight from about 5,000 Da to about 50,000 Da, containing a moiety for adduction to the enzyme. Polyalkylene glycols from 2 to 5 carbon atoms, exemplified by polyethylene glycol, are suitable molecules for adduction to the enzyme. Other suitable large organic molecules include polymers of a single amino acid such as: poly-alanine; poly-glycine; and poly-lysine. Alternatively, large organic polymers such as polyethylenes and poly-vinyls can be used. Furthermore, natural human proteins such as Fab fragments from antibodies can be suitable large organic molecules.

Each adducted large organic molecule imparts a large increase in rotational size of the enzyme while not adding any reactive moieties. One method of large organic molecule adduction to the fibrinolytic enzyme is exemplified by covalent attachment through an NHS ester included in the modifying large organic molecule. An NHS ester reacts with the ε-amino groups of surface lysine residues of fibrolase or any other venom fibrinolytic enzyme to yield a covalent amide linkage.

The method for the construction of one type of size modified fibrinolytic enzyme is detailed in the following sections. Also included are the details pertaining to the specific assays we have performed to determine the extent of size modifying agent adduction on retention of fibrinolytic enzyme activity.

BRIEF DESCRIPTION OF THE DRAWINGS

FIG. 1 is a covalent adduction of N-hydroxy-succinimide containing polyethylene glycol to a fibrinolytic enzyme;

FIG. 2 is a time course of adduction by NHS-PEG to fibrolase analyzed by SDS-PAGE. Lane A, is 0 minute reaction (control). Lanes B–F, correspond to reaction times of 2, 4, 6, 8 and 10 minutes. Lane M, MW are standards;

FIG. 3 shows the separation of mono-PEGylated fibrolase derivative on molecular sieve column, TSK gel SW3000-XL. 2.5×60 cm column eluted isocratically at 2 ml/min;

FIG. 4 is a three-dimensional model of fibrolase based on the x-ray structures of two closely related members of the metzincin family;

FIG. 5 shows a synthetic fluorescence quenched octapeptide substrate for fibrolase;

FIG. 6 shows the cleavage of fluorogenic octapeptide by fibrolase; and

FIG. 7 shows the rate of interaction between fibrolase and α2M as measured by evolution of TNS fluorescence: a) curve showing a saturation level of TNS interacting with a fibrolase-α2M complex; and b) shows the rapid interaction between TNS and the complex.

DETAILED DESCRIPTION OF THE INVENTION

Methods of Modified Fibrinolytic Enzyme Construction and Activity Determination

A. Purification of native fibrolase: Crude *Agkistridon contortrix contortrix* (southern copperhead) venom is composed of a number of different proteins each with a distinct activity. Fibrolase is one of the most abundant proteins in the venom. The methodology for the purification of fibrolase has been published by the Markland laboratory [Loayza, S. L., et al., *J. Chromatog.* B, 662:227–243] (1994). This is a fairly simple three step chromatographic purification employing a different type of high performance liquid chromatography (HPLC) at each step. The first step is hydrophobic interaction HPLC where fibrolase is separated from the bulk of the other proteins in the applied sample. Hydroxylapatite (HAP) HPLC allows for near final purification. Samples containing fibrinolytic activity from the HAP column contain only a single band with a molecular weight of 23 kDa when analyzed by sodium dodecyl sulfate-polyacrylamide gel electrophoresis (SDS-PAGE). The final separation on a PolyCAT-A cation exchange HPLC column separates two different isoforms of fibrolase. Both isoforms possess identical thrombolytic activity when tested in vitro. The difference between these two isoforms is a truncation of a glutamine residue from the amino-terminus of one of the two isoforms.

Figure 2:
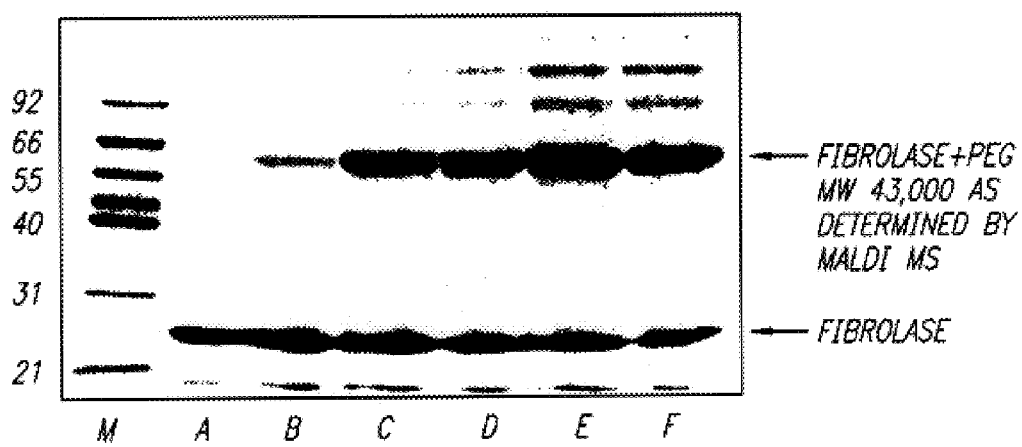
Figure 3:
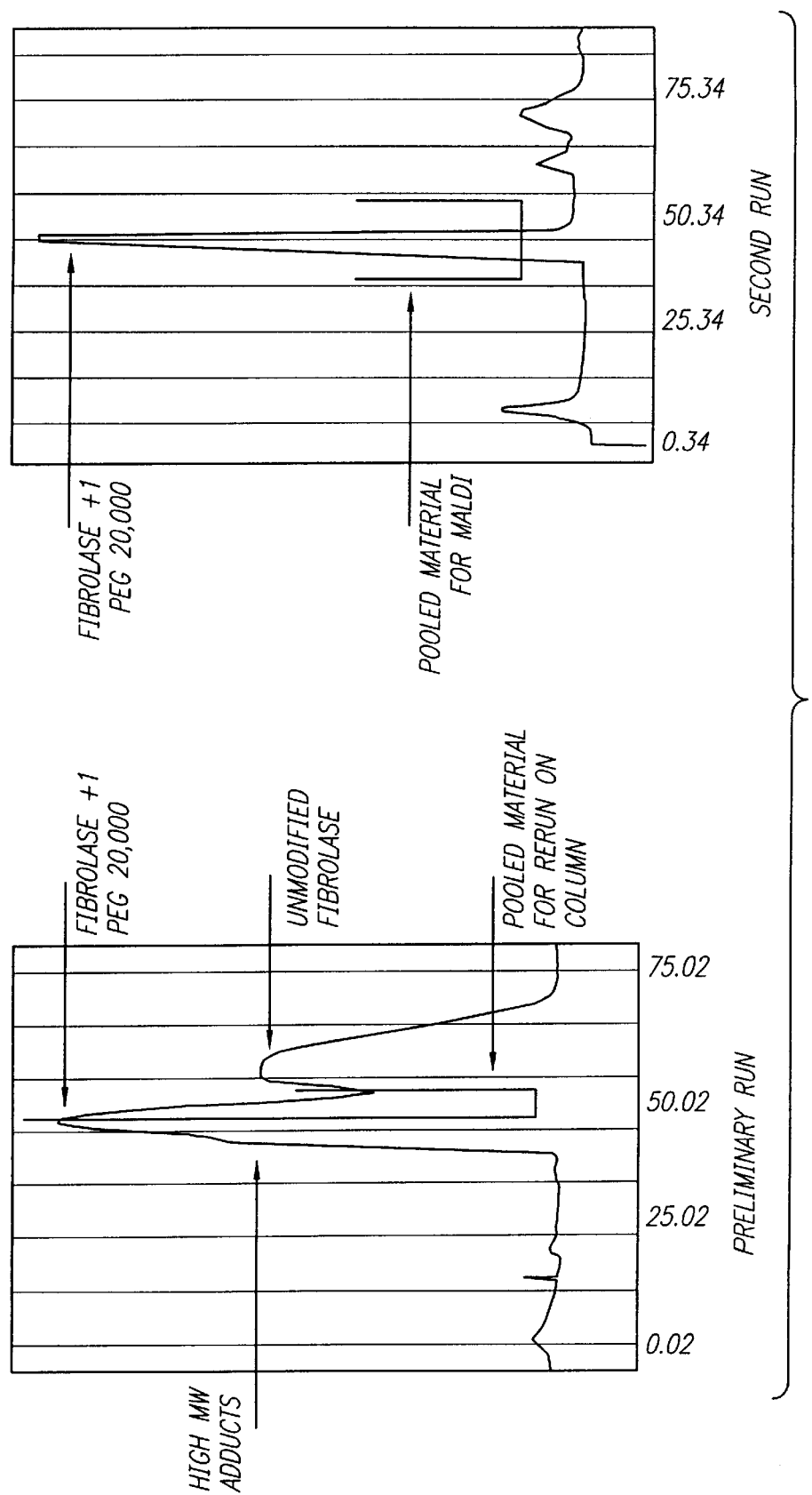

B. Method for Altering the Size of Fibrolase Attachment of a Water Soluble NHS Containing Large Organic Molecule: There are commercially available activated polyethylene glycols (PEG) that contain an N-hydroxy succinimide (NHS) ester which can be adducted to primary amines; see FIG. 1 [Clark, R., et al., *Journal of Biological Chemistry*, 271(36):21969–21977 (1996)]. In that a-amino groups in proteins are not always available for adduction, the $\epsilon$-amino groups of lysine's are generally used for modification. NHS ester adduction has been successfully used for the modification of fibrolase, resulting in the attachment of polyethylene glycols of molecular weights from about 5,000 Da to about 50,000 Da, preferably from about 10,000 Da to about 30,000 Da, to surface lysine residue(s) (unpublished data). The PEGylated fibrolase is created through the reaction of PEG of the desired molecular mass with fibrolase in different stoichiometries depending on the extent of PEGylation desired. We found by varying the time of reaction and molar ratio of PEG to fibrolase, that a molar ratio of 10:1, PEG (mw 20,000) to fibrolase, reacted for 10 minutes at room temperature to yield a number of different PEGylated species of fibrolase including an abundant form with a molecular weight of 43,331 Da as determined by matrix assisted laser desorption ionization mass spectrometry (MALDI-MS) corresponding to the adduction of one PEG molecule to each molecule of fibrolase. This is shown in FIG. 2, wherein reaction conditions buffers and temperature are described in FIG. 1, stoichiometry of reactants 10:1 SPA-PEG to native fibrolase. When analyzed on SDS-PAGE, the product of the PEGylation reaction, the modified fibrolase, migrated aberrantly from that expected for a globular protein but exists as a single primary band. The predominant 43 kDa form of the modified protein is purified by size exclusion chromatography, using HPLC (SW3000-XL column) which separates by size proteins between 10 kDa and 150 kDa. See FIG. 3; two passes over this column yielded a homogenous solution of PEGylated fibrolase MW 43 kDa, determined by MALDI-MS. The running conditions for the 2.5×60 cm column involve isocratic elution with 50 mM HEPES, pH 7.4, 147 mM NaCl at a flow rate of 2 ml/min. On the first pass over the sizing column a near homogenous preparation of the predominant form of the PEGylated fibrinolytic enzyme is achieved. Final purification is carried out by a second run through the same sizing column using the same running conditions.

Figure 4:

C. Determination of Stoichiometry and Position of PEG Attachment: The structure of fibrolase has been modeled based on the high degree of homology with other proteins of the adamalysin sub-family, whose x-ray structure are known [Stocker, W., et al., *Protein Sci.,* 4(5):823–40 (1995)]. See FIG. 4; surface lysine residues, points of attachment for the SPA-PEG are indicated in magenta and the active site histidine residues are highlighted in yellow. The putative active site of fibrolase contains three histidine residues as well as a zinc atom and a methonine turn, the signature motifs of this class of enzyme. Understanding how the addition of PEG or other large organic molecule chains effects the structure and stereochemistry of the active site aids in the determination of how alteration of the molecular weight through the adduction of an NHS containing large organic molecule effects enzymatic activity.

There are seven lysine residues in the primary structure of fibrolase. From our model of fibrolase, each of these lysine residues lies outside the active site, sufficiently so that modification of the residue apparently has no effect on the activity of the enzyme (Bolger et al., in preparation). Purified material containing the PEG adduct(s) has been analyzed on SDS-PAGE to determine the homogeneity of the PEGylated preparation, but the true mass of the modified fibrolase has been determined through mass spectrometry. Exact mass determination of the adducted species allows for a calculation of the number of PEG molecules attached to each species of fibrolase. The position of adduction in fibrolase can be determined by site specific enzymatic cleavage of the modified protein followed by amino acid analysis and peptide sequencing of the resultant peptide fragments.

In brief, to determine the positions of PEG or other large molecular weight organic molecule adduction, both natural fibrolase and the modified material obtained following molecular sieve HPLC purification, as described earlier, are reduced and alkylated using standard procedures [Guan, A. L., et al., *Arch. Biochem. Biophys.,* 289:197–207 (1991)]. Separately, PEGylated and native enzyme are then digested with TPCK treated trypsin. The digestion products are separated by reverse phase HPLC using a C18 column with an increasing gradient of acetonitrile in 0.1% trifluoroacetic acid. Peptides that differ between the digests of the PEGylated and native proteins are assayed for amino acid content and sequenced, if necessary, to identify the position of the adduction in the known primary structure of fibrolase. This process is aided by our knowledge that the attachment sites for the NHS-PEG can only be lysine residue(s). Digestion peptides are also analyzed by mass spectrometry. This yields the same information as the tryptic digest followed by the amino acid analysis, but additionally allows for the determination of the exact molecular weight of the adducted PEG peptide. The most desirable fibrolase derivative is one which possesses close to 100% of natural fibrinolytic activity while having a depressed interaction with $\alpha 2M$ and any other blood borne proteinase inhibitors which would slow down the rate of clearance from the circulatory system. The information concerning the number and placement of adducts along with data concerning activity and inhibition allows for the selection of the modified enzyme that is the most useful thrombolytic agent requiring the smallest therapeutic dose.

D. Testing for fibrinolytic activity in vitro: Once the extent of large organic molecule-protein adduction was determined, retention of enzymatic activity by the modified fibrolase was determined by in vitro assays comparing the fibrinolytic efficacy of both PEGylated and native fibrolase alone and in the presence of α2M.

Protein in the eluent peaks from the size exclusion HPLC purification of the large organic molecule modified enzyme has been assayed for fibrinolytic activity utilizing both an assay for non-specific proteolysis, the colorometric azocasein assay, and the fibrin specific fibrin plate method as described by Bajwa et al. [Bajwa, S. S., et al., Toxicon, 18:285–290 (1980)] (Table 1).

TABLE 1

Proteolytic (Azocasein hydrolysis) and Fibrinolytic Activity of Native and PEGylated Fibrolase

| Enzyme Species | Specific Activity | | | |
|---|---|---|---|---|
| | Azocasein (units/µg) | % | Human Fibrin (units/µg) | % |
| Fibrolase | 1.26 ± 0.03 | 100 | 11.3 ± 0.03 | 100 |
| PEGylated Fibrolase | 1.20 ± 0.03 | 94 | 10.9 ± 0.05 | 97 |

The latter of the two methods for determining fibrinolytic activity is specific for the degradation of fibrin. Quantitation of specific activity in the fibrin plate method is made through a calculation of the area of proteolysis on the fibrin plate per unit weight of protein. Through the comparison between large organic molecule modified and unmodified fibrolase it is evident that there is no loss of proteolytic activity upon attachment of PEG to fibrolase through the NHS crosslinking method.

Figure 5:
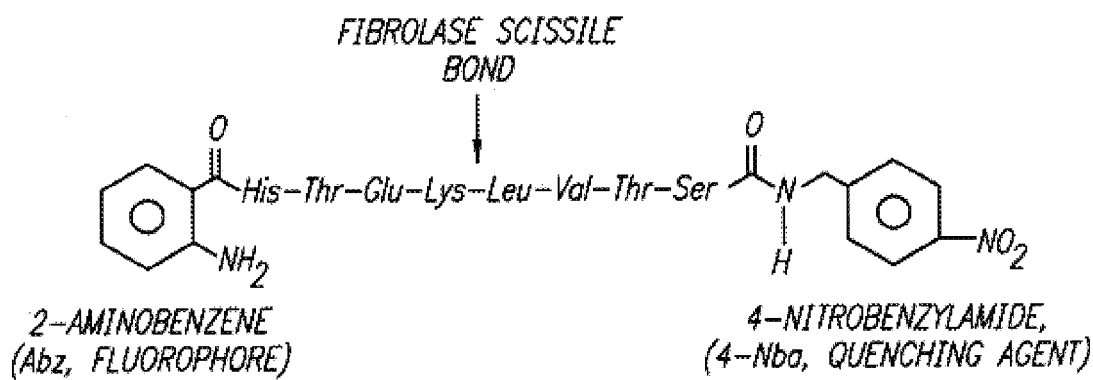

While it is apparent that fibrinolytic activity is retained by the PEGylated fibrolase, the effect of PEGylation on enzyme kinetics are of interest. Interaction kinetics between fibrolase, PEGylated or unmodified, and a synthetic fluorescence quenched octapeptide substrate containing the scissile bond cleaved by fibrolase in the α-chain of fibrin is determined by monitoring the change in fluorescence over reaction time. See FIG. 5; the fibrolase scissile bond between the Lys and Leu cuts the peptide in half. This in turn increases the distance between the fluorescent Abz and the 4-Nba, quenching group yielding a rise in fluorescent signal. The rate of the rise in signal is proportional to the rate of cleavage of the peptide. The fluorophore upon excitation by the proper wavelength of light yields a characteristic fluorescence signal but when in the proper geometry with a quenching group the fluorescence signal is not emitted. In our synthetic peptide the quencher completely absorbs the energy required for a signal from the fluorophore when both fluorophore and quencher are attached to the peptide. When the peptide is cleaved, the distance between the fluorophore and the quenching group becomes too large and the energy is not absorbed but released as a fluorescence signal. The rate at which the fluorescence signal increases is proportional to the hydrolytic rate of the synthetic peptide by the enzyme being tested.

Figure 6:
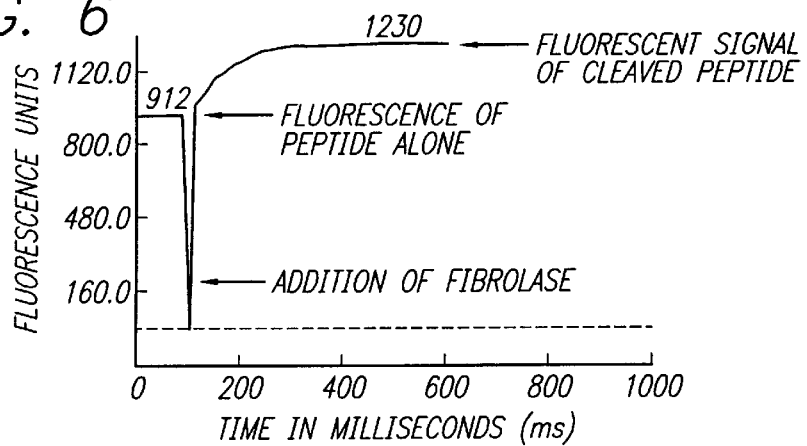

Comparison between the rate of cleavage by the PEGylated and native fibrolase determines whether the proteolytic activity of the modified protein is significantly altered from that of the native material. Some data indicate that fibrolase cleavage of the synthetic peptide is very rapid. See FIG. 6; a synthetic peptide containing the fluorophore and quencher (2-aminobenzene and 4-nitro benzyl amide, respectively) emits a higher fluorescent signal when the fibrolase scissle bond is cleaved. The rate of increase in the fluorescent signal is proportional to the rate of cleavage of the peptide. In this experiment equal molar amounts if fibrolase and peptide were mixed in a stopped-flow fluorometer and the rate of cleavage is evidenced by the rate of change in signal. The sharp drop and recovery of signal with the addition of the sample are an artifact of the system.

Figure 7:
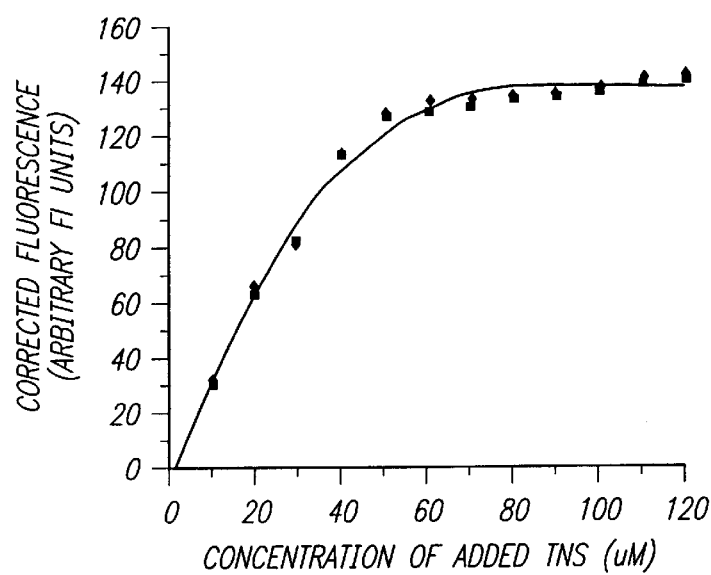
Figure 7:
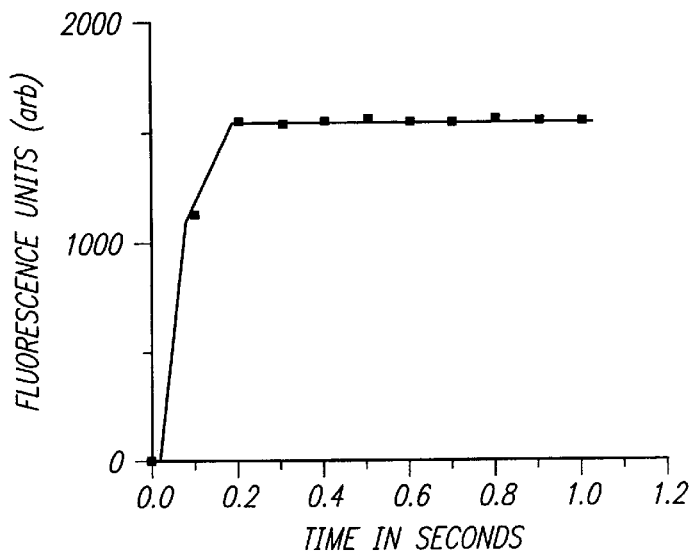

E. Loss of fibrinolytic activity through interaction with α2M: Having established the effect of adduction on fibrinolytic activity, the rate of interaction between adducted fibrolase and α2M has been determined and compared with the interaction with native fibrolase. As stated previously the main means of fibrolase clearance from the circulatory system is α2M. The interaction of α2M and fibrolase is mediated by the cleavage of a peptide bond in the bait region of α2M by fibrolase. This cleavage leads to a conformational change in α2M which irreversibly captures the agent which cleaved the bait region. In SDS-PAGE the cleavage, which causes a conformational change in α2M, can be visualized by the degradation of the monomeric (180 kDa) α2M to two pieces of approximately 90 kDa each [Baramova, E. N., et al., Biochemistry, 29:1069–1074 (1990)]. SDS-PAGE can be used to observe the kinetics of binding of fibrolase to α2M, but in the case of native fibrolase the in vitro interaction between fibrolase and α2M is so rapid that the kinetic parameters cannot be measured (unpublished data). While SDS-PAGE is an important tool for the observation of the binding of either modified or native fibrolase to α2M, the interaction of the fluorescent compound 2-(p-toluidinyl) naphthalene-6-sulfonic acid (TNS) with conformationally changed α2M can be used to determine the kinetics of the interaction. TNS binds to native α2M with very low affinity, but the affinity increases dramatically when the conformation of α2M is changed by cleavage in the bait region [Strickland, D. K., et al, Biochemistry, 30:2797–2803 (1991)]. The kinetics of this cleavage can be monitored by recording the change in the fluorescence signal of TNS; as α2M is cleaved the signal increases [Bjork, I., et al., Biochemistry, 28(4):1568–1573 (1989)]. One can compare the association rates of α2M with modified and unmodified fibrolase to yield the kinetics of this interaction; see FIG. 7.

Unmodified fibrolase is quickly and efficiently inactivated by α2M. An assay was performed to determine the differences in inhibition of the PEGylated and native fibrolase by α2M. Both forms of fibrolase at known concentration were incubated with known amounts of α2M, either purified or in plasma (concentration of α2M in plasma was assumed to be the literature value of 2.9 µM). The mixtures were incubated for 45 seconds at 37° C. and then placed directly on the fibrin plate. As is evidenced by Table 2, native fibrolase is effectively inactivated by either purified or plasma forms of α2M. PEGylated fibrolase shows no loss of activity in the presence of either form of α2M.

TABLE 2

Fibrinolytic Activity of Native and PEGylated Fibrolase
Incubated in the Presence of Saline, Human Plasma or
Purified Human α2 Macroglobulin using fibrin plate lysis

| Enzyme Species | Fibrinolytic clearance in mm$^2$ by fibrolase or PEGylated fibrolase incubated in the presence of: | | |
|---|---|---|---|
| | + Saline | + Human Plasma | + α2-Macroglobulin |
| Native Fibrolase | 11.3 ± 0.2 | 0.0 ± 0.2 | 0.0 ± 0.2 |
| PEGylated Fibrolase | 10.9 ± 0.2 | 10.4 ± 0.2 | 10.1 ± 0.2 |

EXAMPLES

Example I

Methods

Fibrolase was isolated from crude *Agkistridon contortrix contortrix* venom via a three step HPLC procedure [Loyaza, et al. (1994)]. The purified enzyme was then reacted with 20 kDa PEG containing a succinimide ester functional group. The ester reacted readily with the ε-amino group of surface lysine residues of fibrolase, of which there are seven. After reaction, PEGylated fibrolase was analyzed for alteration in molecular size by SDS-PAGE. The different molecular weight forms of the PEGylated enzyme were resolved by molecular sieve chromatography. PEGylated fibrolase was tested for fibrinolytic activity by fibrin plate assay, and the kinetics of interaction with α2M was determined by a fluorescent assay. The extent of interaction was monitored by SDS-PAGE analysis of fibrolase-induced α2M cleavage.

Results

SDS-PAGE analysis of the PEGylation reaction showed that there were approximately seven different PEGylated species of fibrolase each differing by an integer of 20 kDa. All of the native fibrolase was consumed in this reaction and varying the time of reaction yielded different quantities of each of the different species. PEGylated, material retained close to 100% of native fibrinolytic activity and had a greatly diminished interaction with α2M as detected by SDS-PAGE.

Example II

Methods

Fibrolase was isolated from crude *Agkistridon contortrix contortrix* venom via a three step HPLC procedure as described in Example I. Purified enzyme was then reacted with 20 kDa PEG containing a succinimide ester functional group. The ester reacted readily with the ε-amino group of the seven surface lysine residues of fibrolase. Reactions containing a 10:1 stoichiometry of NHS-PEG to fibrolase were allowed to proceed for 10 minutes before being stopped by the addition of excess methylamine. After completion of the reaction, a single species of PEGylated fibrolase was purified by a two-step molecular sieve HPLC procedure. MALDI-MS was used to determine the molecular weight of the PEGylated fibrolase. The effect of PEGylation on the inhibition of fibrinolytic activity of α2M was determined using the fibrin plate assay, following brief incubation in saline (control), human α2M, or plasma of different species.

Results

Following molecular sieve HPLC, analysis of purified PEGylated fibrolase by SDS-PAGE revealed a single predominant band with an apparent molecular weight of 63 kDa. When subjected to MALDI-MS this band had been determined to have a MW of 43 kDa, corresponding to the adduction of a single PEG 20,000 Da molecule to fibrolase. PEGylated material retained close to 100% of native fibrinolytic activity. In the presence of α2M, either purified or in plasma, fibrinolytic activity in native protein completely inhibited following a 45 second incubation, whereas PEGylated fibrolase retained close to 100% of its activity under the same conditions.

Examples III–XIII

The procedure of Example II can be followed by substituting the following large organic molecules for the 20 kDa PEG:

| Example | Substitute |
|---|---|
| III | 5 kDa Poly ethylene glycol |
| IV | 50 kDa Poly ethylene glycol |
| V | 10 kDa Poly ethylene glycol |
| VI | 30 kDa Poly ethylene glycol |
| VII | 40 kDa Poly propyl glycol |
| VIII | 12 kDa Poly butyl glycol |
| IX | 18 kDa Poly pentyl glycol |
| X | 24 kDa Poly-alanine glycol |
| XI | 30 kDa Poly-glycine glycol |
| XII | 40 kDa Poly-lysine glycol |
| XIII | 50 kDa Poly-vinyl glycol |

What is claimed is:

1. A size modified fibrinolytic enzyme of the adamalysin sub-family, wherein the size of the enzyme is modified by covalent attachment of at least one large organic molecule to the enzyme and the modified enzyme possesses about the same proteolytic activity as native enzyme.

2. The enzyme of claim 1, wherein the fibrinolytic enzyme is fibrolase.

3. The enzyme of claim 1, wherein the large organic molecule is water soluble.

4. The enzyme of claim 1, wherein the large organic molecule is a polymer molecule.

5. The enzyme of claim 4, wherein the polymer molecule is polyethylene glycol.

6. The enzyme of claim 2, wherein about one to about seven polymer molecules are attached to the enzyme.

7. A method for modifying the size of a fibrinolytic enzyme of the adamalysin sub-family comprising the steps of:
   (a) combining the fibrinolytic enzyme with a large organic molecule containing an adduction moiety; and
   (b) attaching at least one large organic molecule to the enzyme so that the enzyme is modified but still possesses about the same proteolytic activity as native enzyme.

8. The method of claim 7, wherein the large organic molecule is a polymer molecule.

9. The method of claim 7, wherein the adduction moiety is a succinimide ester.

10. The method of claim 7, wherein the fibrinolytic enzyme is fibrolase.

11. The method of claim 8, wherein the polymer molecule is water soluble.

12. The method of claim 11, wherein the polymer molecule is polyethylene glycol.

13. The method of claim 10, wherein about one to about seven polymer molecules are attached to the enzyme.

14. The method of claim 10, wherein a molar excess of the polymer is combined with the enzyme.

* * * * *

UNITED STATES PATENT AND TRADEMARK OFFICE
CERTIFICATE OF CORRECTION

PATENT NO.    : 6,214,594 B1
DATED         : April 10, 2001
INVENTOR(S)   : Markland et al.

It is certified that error appears in the above-identified patent and that said Letters Patent is hereby corrected as shown below:

<u>Title page,</u>
Item [73], Assignee, should read -- University of Southern California, University Park, Los Angeles, CA (US) --.

Signed and Sealed this

Twenty-second Day of July, 2003

JAMES E. ROGAN
*Director of the United States Patent and Trademark Office*